(12) United States Patent
Eh et al.

(10) Patent No.: US 8,268,772 B2
(45) Date of Patent: Sep. 18, 2012

(54) DEPOT PREPARATIONS

(75) Inventors: Marcus Eh, Holzminden (DE); Horst Surburg, Holzminden (DE); Steffen Sonnenberg, Holzminden (DE)

(73) Assignee: Symrise AG, Holzminden (DE)

( * ) Notice: Subject to any disclaimer, the term of this patent is extended or adjusted under 35 U.S.C. 154(b) by 1286 days.

(21) Appl. No.: 11/325,941

(22) Filed: Jan. 5, 2006

(65) Prior Publication Data

US 2006/0111269 A1 May 25, 2006

Related U.S. Application Data

(62) Division of application No. 10/222,301, filed on Aug. 16, 2002, now abandoned.

(30) Foreign Application Priority Data

Aug. 20, 2001 (DE) .................. 101 40 786

(51) Int. Cl.
*A61Q 5/10* (2006.01)
(52) U.S. Cl. .............. 512/27; 512/26; 512/1; 8/426; 8/429
(58) Field of Classification Search ............. 512/1, 27, 512/26; 8/426, 429
See application file for complete search history.

(56) References Cited

U.S. PATENT DOCUMENTS

| 3,023,247 A | 2/1962 | Scriabine |
| 3,250,681 A * | 5/1966 | Cahill, Jr. et al. ............ 504/157 |
| 4,395,430 A | 7/1983 | Byrne et al. |
| 4,800,233 A | 1/1989 | Simmons |
| 4,910,347 A | 3/1990 | Simmons |
| 5,744,637 A * | 4/1998 | Tustin et al. ............ 560/238 |
| 6,004,355 A * | 12/1999 | Dias et al. ............ 8/406 |
| 6,106,849 A * | 8/2000 | Malkan et al. ............ 424/401 |

FOREIGN PATENT DOCUMENTS

| EP | 0456932 A1 | 11/1991 |
| EP | 0963974 A1 | 3/1999 |
| GB | 2195125 | 3/1988 |
| JP | 55-133327 | * 10/1980 |
| JP | 62021772 A | 1/1987 |

OTHER PUBLICATIONS

Chandra et al., An Efficient Method for Diacetylation of Aldehydes, Synlett. 2000, No. 3, pp. 359-360.
Heck, R., Organomet. Chem Synth., 1, pp. 455-465 (1972) (XP-002230705).
Wegschneider, S., Montash Chem. 30, p. 841 (1909) (XP-002230708).
Zhang, L. et al., Constituents of essential oils in lonicera japonica, Zhongguo Yaoke Daxue Xuebao, vol. 25, No. 3, pp. 184-187, 1994.
Ogibin, Y. et al., Bull. Acad. Sci. USSR Div. Chem. Sci., pp. 361-363, 1965.
Wakayama, et al., XP002230704, 72, p. 275, 1951.
Semmler, Chem. Ber., 42, p. 1161, 1909.
Sumida, N. et al., Syn. Lett., 12, pp. 1921-1922.

* cited by examiner

*Primary Examiner* — Douglas McGinty
(74) *Attorney, Agent, or Firm* — Duane Morris LLP; J. Rodman Steele, Jr.; Gregory M. Lefkowitz

(57) ABSTRACT

The present invention relates to depot preparations for the targeted release of an aldehyde together with two carboxylic acids, where the released aldehydes are organoleptic substances, specifically fragrances or flavorings, and these depot preparations are prepared by reacting aldehydes with carboxylic anhydrides.

18 Claims, No Drawings

DEPOT PREPARATIONS

CROSS REFERENCE TO RELATED APPLICATION

This application is a Divisional Application of prior parent application Ser. No. 10/222,301 filed on Aug. 16, 2002, now abandoned. Priority is claimed from Aug. 20, 2001, based on German Application No. 101 40 786.6.

FIELD OF THE INVENTION

The present invention relates to depot preparations or delivery systems for the targeted release of an aldehyde with two carboxylic acids. The released aldehydes are organoleptic substances, which are useful as fragrances or flavorings. The depot preparations can be prepared by reacting aldehydes with carboxylic anhydrides.

BACKGROUND OF THE INVENTION

The method for perfuming consumer articles involves mixing the perfume oil containing fragrances directly with the product. The problems, which arise with this process, are that readily volatile substances are partially or completely lost as a result of evaporation during incorporation into the product or during storage. In addition, numerous substances, and aldehydes in particular, are unstable under the given conditions, which leads to partial or complete decomposition of these molecules. The consequence of this is that all substances, which underlie the problems described above, can, in sensory terms, only be weakly perceived or cannot be perceived at all. In some cases this may lead to a change in the overall odor impression of the composition.

WO 94/06441 discloses acetals, ketals and specific ortho esters as depot preparations, which are stable in basic media. In acidic media, such as, for example, upon contact with the skin, hydrolysis occurs, releasing alcohols and ketones.

A depot preparation for the release of aldehydes, specifically citral, in foods and here specifically in alcoholic or nonalcoholic beverages is described in WO 00/04009. These are dicarboalkoxydioxolans, which are obtainable by acetylation from an aldehyde and a tartaric acid derivative. In aqueous acidic alcoholic and nonalcoholic beverages these preparations have a longer half-life than comparable acetals.

WO 00/38616 discloses a cyclic dioxaketone, which, after hydrolysis, simultaneously releases an aldehyde or ketone and a hydroxy-carboxylic acid. These compounds are prepared by reacting the corresponding hydroxycarboxylic acid with the aldehyde or ketone with the addition of catalytic amounts of acid in the water separator. Preference is given to aldehydes or ketones with fragrance properties and .alpha.-hydroxy-carboxylic acids or ring-substituted benzoic acids.

However, none of the above-mentioned depot preparations has the ability to simultaneously release the fragrance component in addition to two further compounds. Furthermore, the problems, which arise with the conventional perfuming of consumer articles (evaporation during storage, instability etc.), are solved by the depot preparation according to the present invention.

SUMMARY OF THE INVENTION

The present invention provides depot preparations containing at least one compound of the formula (I)

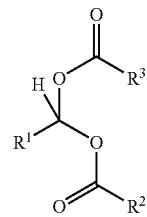

in which
R.sup.1, R.sup.2 and R.sup.3, independently, are an organic radical having 1 to 30 carbon atoms, and the compound of the formula (I), after hydrolysis or enzymatic cleavage, releases an aldehyde and two carboxylic acids.

DETAILED DESCRIPTION OF THE INVENTION

Preferably the present inventions contains compounds of the formula (I) in which $R^1$ is a saturated or unsaturated, linear or branched, alicyclic or aromatic radical having 1 to 18 carbon atoms, which may optionally also contain heteroatoms, $R^2$ and $R^3$, independently, are a saturated or unsaturated, linear or branched, alicyclic or aromatic radical having 1 to 22 carbon atoms, which may optionally also contain heteroatoms and which may optionally be substituted by ionic substituents, or in which $R^2$ and $R^3$ together form a saturated or unsaturated, branched or unbranched, carbocyclic or aromatic ring of 3 to 10 carbon atoms, preferably of 4 to 8 carbon atoms.

Preferred heteroatoms include oxygen and sulfur. More preferably the heteroatoms are oxygen.

Examples of ionic substituents include $—CO_2M$ or $—OCO_2M$, where M is an alkali metal.

The acylals of the formula (I), according to the present invention, decompose after aqueous hydrolysis, preferably in alkaline aqueous medium with a pH of $\geq 8$, and also in acidic aqueous medium with a pH of <3, more preferably the alkaline hydrolysis has a pH range from 9 to 13 and the acidic hydrolysis has a pH range from 0 to 2.5, so that an aldehyde and two carboxylic acids can be released which in turn releases the fragrance or flavoring and then can adhere to substrates. On the other hand, the acylals of the formula (I), according to the present invention, decompose after enzymatic cleavage, releasing an aldehyde and two carboxylic acids, which in turn releases the fragrance, or flavoring and then can attach to substrates.

Surprisingly, the release rate can be controlled via the radicals $R^2$ and $R^3$, depending on $R^1$, such that acylals with small and narrow radicals $R^2$ and $R^3$ have short half-lives, while voluminous and long-chain radicals $R^2$ and $R^3$ increase the half-life of the acylals. This is significant in as much as acylals of the formula (I) with different release profiles can thus be prepared. Accordingly, the depot preparation and the formulation can be matched to one another as regards respective radicals or ingredients in order to achieve an application-oriented release as a result of controlled release or controlled adhesion/transfer.

The enzymatic cleavage can preferably be carried out by esterases or lipases.

Preferably, the aldehyde released from the compound of the formula (I) has a molecular weight of from 100 to 350 g/mol and more preferably from 120 to 270 g/mol. It is also preferred if the released aldehyde is a fragrance or flavoring.

Nonlimiting examples of aldehydes which can be released following cleavage of the depot preparation according to the present invention include: phenylacetaldehyde, p-methylphenylacetaldehyde, p-isopropyl-phenylacetaldehyde, methylnonylacetaldehyde, phenylpropanal, 3-(4-t-butylphenyl)-2-methylpropanal (lilial), 3-(4-t-butylphenyl)propana-1 (bourgeonal), 3-(4-methoxyphenyl)-2-methylpropanal (canthoxal), 3-(4-isopropylphenyl)-2-methylpropanal (cymal), 3-(3,4-methylenedioxyphen-yl)-2-methylpropanal (helional), 3-(4-ethylphenyl)-2,2-dimethylpropanal (floralozone), phenylbutanal, 3-methyl-5-phenylpentanal, hexanal, trans-2-hexenal, cis-hex-3-enal, heptanal, cis-4-heptenal, 2-ethyl-2-heptenal, 2,6-dimethyl-5-heptenal (melonal), 2,4-heptadienal, octanal, 2-octenal, 3,7-dimethyloctanal, 3,7-dimethyl-2,6-octadien-1-al, 3,7-dimethyl-2,6-octadien-3-al, 3,7-dimethyl-6-octenal (citronellal), 3,7-dimethyl-7-hydroxy-octan-1-al (hydroxycitronellal), nonanal, 6-nonenal, 2,4-nonadienal, 2,6-nonadienal, decanal, 2-methyldecanal, 4-decenal, 9-decenal, 2,4-decadienal, undecanal, 2-methyldecanal, 2-methylundecanal, 2,6,10-trimethyl-9-undecenal (adoxal), undec-10-enylaldehyde, undec-8-enanal, dodecanal, tridecanal, tetradecanal, anisaldehyde, cinnamal-dehyde, .alpha.-amylcinnamaldehyde, .alpha.-hexylcinnamaldehyde, methoxy-cinnamaldehyde, isocyclocitral, citronellyloxyacetaldehyde, cortexal-dehyde, cuminaldehyde, cyclamenaldehyde, florhydral, heliotropin, hydratropaldehyde, vanillin, ethylvanillin, benzaldehyde, p-methylbenz-aldehyde, 3,4-dimethoxybenzaldehyde, 3- and 4-(4-hydroxy-4-methyl-pentyl)-3-cycloh-exene-1-carboxaldehyde (lyral), 2,4-dimethyl-3-cyclohexene -1-carboxaldehyde (triplal), I-methyl-3-(4-methylpentyl)-3-cyclohexenecarboxaldehyde (vernaldehyde) or p-methylphenoxyacetaldehyd-e (Xi aidehyde).

Nonlimiting examples of carboxylic acids which can be released following cleavage of the depot preparation according to the present invention include: unsubstituted saturated monocarboxylic acids (e.g. acetic acid, propionic acid, butyric acid, valeric acid, capric acid, caprylic acid, pelargonic acid, capric acid, lauric acid, myristic acid, palmitic acid, stearic acid); dialkyl-substituted acetic acids (e.g. 2-butyloctanoic acid, 2-butyldecanoic acid, 2-hexyloctanoic acid, 2-hexyldecanoic acid); mono- or polyunsaturated monocarboxylic acids (e.g. oleic acid, linoleic acid, (.alpha.-linolenic acid, (.gamma.-linolenic acid); alkyne-, alkadiyne- or alkatriyne carboxylic acids (e.g. non-8-ynoic acid, dec-9-ynoic acid, tridec-9-ynoic acid, 13-methyltetradec-9-ynoic acid, pentadec-6-ynoic acid, pentadec-7-ynoic acid, hexadec-9-ynoic acid, 15-methylhexadec-9-ynoic acid, heptadec-2-ynoic acid, heptadec-9-ynoic acid, octadec-12-ynoic acid, octadec-6,12-diynoic acid, nonadec-9-ynoic acid); .alpha.-hydroxycarboxylic acids (e.g. .alpha.-hydroxyvaleric acid, alpha.-hydroxycaproic acid, .alpha.-hydroxycaprylic acid, alpha.-hydroxypelargonic acid, .alpha.-hydroxycapric acid, alpha.-hydroxylauric acid, alpha.-hydroxymyristic acid, alpha.-hydroxypalmitic acid, alpha.-hydroxypalmitic acid); unsubstituted alpha.,.omega.-alkanedicarb-oxylic acids (e.g. malonic acid, succinic acid, glutaric acid, adipic acid, pimelic acid, suberic acid, azelaic acid).

Preferably, the depot preparation according to the present invention includes acylals of the formula (I) which have poor solubility in water and thus have a relatively large tendency to attach to substrates, or to accumulate in the headspace above an aqueous solution. Therefore, it is preferable for the acylals of the formula (I) according to the present invention to have a lower solubility in water than the carboxylic acids which are released so that better attachment of the carboxylic acids to the substrate can arise, or accumulation in the headspace above the aqueous phase takes place. Solubilities can be measured directly or can be determined more easily using octanol/water partition coefficients (log P value). The log P value is an established parameter for determining lipophilicity in the literature (A. Leo, C. Hansch and D. Elkins, Chem. Rev., 71, 1971, 525-616; C. Hansch, J. E. Quinlan, G. L. Lawrence, J. Org. Chem., 33, 1968, 347-350).

Generally, for molecules with a low log P value, the transition from an aqueous system to a substrate is difficult as such molecules have a tendency to dissolve and be washed away. This applies to acidic compounds. The present invention can overcome this problem because the transition of the carboxylic acid with a low log P value from the aqueous solution to a substrate takes place in the chemically bonded form of the acylals of the formula (I) according to the present invention having a higher log P value. This means that the transfer of a carboxylic acid following release from the depot preparation takes place at a higher rate than the transfer of the free carboxylic acid. Release takes place after subsequent cleavage of the depot preparation according to the present invention.

The controlled release of the aldehyde and of the two carboxylic acids from the depot preparation according to the present invention can be utilized for the treatment (e.g. fragrancing) of a wealth of substrates, such as, for example, hair, human skin, laundry and hard surfaces.

Examples of fragrances or perfume oils with which the depot preparation according to the present invention can be advantageously combined are given, for example, in S. Arctander, Perfume and Flavour Materials, Vol. I and 11, Montclair, N. J., 1969, published privately or K. Bauer, D. Garbe and H. Surburg, Common Fragrance and Flavour Materials, $3^{rd}$ Ed., Wiley-VCH, Weinheim 1997.

Individual examples, which may be mentioned, include: extracts from natural raw materials such as essential oils, concretes, absolutes, resins, resinoids, balsams, tinctures, such as, for example, ambergris tincture; amyris oil; angelica seed oil; angelica root oil; aniseed oil; valerian oil; basil oil; wood moss absolute; bay oil; mugwort oil; benzoin resin; bergamot oil; beeswax absolute; birch tar oil; bitter almond oil; savory oil; bucco leaf oil; cabreuva oil; cade oil; calmus oil; camphor oil; cananga oil; cardamom oil; cascarilla oil; cassia oil; cassia absolute; castoreum absolute; cedar leaf oil; cedarwood oil; cistus oil; citronella oil; lemon oil; copaiva balsam; copaiva balsam oil; coriander oil; costus root oil; cumin oil; cypress oil; davana oil; dill herb oil; dill seed oil; eau de brouts absolute; oakmoss absolute; elemi oil; tarragon oil; eucalyptus citriodora oil; eucalyptus oil; fennel oil; fir-needle oil; galbanum oil; galbanum resin; geranium oil; grapefruit oil; guaiac wood oil; gurjun balsam; gurjun balsam oil; helichrysum absolute; helichrysum oil; ginger oil; iris root absolute; iris root oil; jasmine absolute; calmus oil; blue camomile oil; Roman camomile oil; carrot seed oil; cascarilla oil; pine-needle oil; spearmint oil; caraway oil; labdanum oil; labdanum absolute; labdanum resin; lavandin absolute; lavandin oil; lavender absolute; lavender oil; lemongrass oil; lovage oil; distilled lime oil; pressed lime oil; linaloe oil; litsea cubeba oil; laurel leaf oil; mace oil; marjoram oil; mandarin oil; massoi bark oil; mimosa absolute; musk seed oil; musk tincture; clary sage oil; nutmeg oil; myrrh absolute; myrrh oil; myrtle oil; clove leaf oil; clove flower oil; neroli oil; olibanum absolute; olibanum oil; opopanax oil; orange-flower absolute; orange oil; origanum oil; palmarosa oil; patchouli oil; perilla oil; Peruvian balsam oil; parsley leaf oil; parsley seed oil; petitgrain oil; peppermint oil; pepper oil;

pimento oil; pine oil; pennyroyal oil; rose absolute; rosewood oil; rose oil; rosemary oil; Dalmatian sage oil; Spanish sage oil; sandalwood oil; celery seed oil; spike lavender oil; Japanese anise oil; styrax oil; tagetes oil; fir-needle oil; tea-tree oil; turpentine oil; thyme oil; Tolu balsam; tonka absolute; tuberose absolute; vanilla extract; violet leaf absolute; verbena oil; vetiver oil; juniper oil; wine lees oil; absinthe oil; wintergreen oil; ylang oil; hyssop oil; civet absolute; cinnamon leaf oil; cinnamon bark oil; and fractions thereof, or ingredients isolated therefrom; individual fragrances from the group of hydrocarbons, such as, for example, 3-carene; alpha.-pinene; .beta.-pinene; alpha.-terpinene; gamma.-terpinene; p-cymene; bisabolene; camphene; caryophyllene; cedrene; farnesene; limonene; longifolene; myrcene; ocimene; valencene; (E,Z)-1,3,5-undecatriene;

of aliphatic alcohols, such as, for example, hexanol; octanol; 3-octanol; 2,6-dimethylheptanol; 2-methylheptanol, 2-methyloctanol; (E)-2-hexenol; (E)- and (Z)-3-hexenol; 1-octen-3-ol; mixture of 3,4,5,6,6-pentamethyl-¾-hepten-2-ol and 3,5,6,6-tetramethyl-4-methylen-eheptan-2-ol; (E,Z)-2,6-nonadienol; 3,7-dimethyl-7-methoxyoctan-2-ol; 9-decenol; 10-undecenol; 4-methyl-3-decen-5-ol; of aliphatic aldehydes and 1,4-dioxacycloalken-2-ones thereof, such as, for example, hexanal; heptanal; octanal; nonanal; decanal; undecanal; dodecanal; tridecanal; 2-methyl-octanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal diethyl acetal; 1,1-dimethoxy-2,2,5-trimethyl-4-hexene; citronellyl oxyacetaldehyde;

of aliphatic ketones and oximes thereof, such as, for example, 2-heptanone; 2-octanone; 3-octanone; 2-nonanone; 5-methyl-3-heptanone; 5-methyl-3-heptanone oxime; 2,4,4,7-tetramethyl-6-octen-3-one; of aliphatic sulphur-containing compounds, such as, for example, 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

of aliphatic nitriles, such as, for example, 2-nonenenitrile; 2-tridecene-nitrile; 2,12-tridecenenitrile; 3,7-dimethyl-2,6-octadienenitrile; 3,7-dimethyl-6-octenenitrile;

of aliphatic carboxylic acids and esters thereof, such as, for example, (E)- and (Z)-3-hexenyl formate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octynoate; methyl 2-nonynoate; allyl 2-isoamyloxyacetate; methyl 3,7-dimethyl-2,6-octadienoate;

of acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and formates, acetates, propionates, isobutyrates, butyrates, isovalerates, pentanoates, hexanoates, crotonates, tiglinates and 3-methyl-2-butenoates thereof;

of acyclic terpene aldehydes and ketones, such as, for example, geranial; neral; citronellal; 7-hydroxy-3,7-dimethyloctanal; 7-methoxy-3,7-dimethyl-octanal; 2,6,10-trimethyl-9-undecenal; geranylacetone; and the dimethyl and diethyl acetals of geranial, neral, 7-hydroxy-3,7-dimethyloctanal;

of cyclic terpene alcohols, such as, for example, menthol; isopulegol; alpha-terpineol; terpinenol-4; menthan-8-ol; menthan-1-ol; menthan-7-ol; borneol; isoborneol; linalool oxide; nopol; cedrol; ambrinol; vetiverol; guaiol; and formates, acetates, propionates, isobutyrates, butyrates, isovalerates, pentanoates, hexanoates, crotonates, tiglinates and 3-methyl-2-butenoates thereof;

of cyclic terpene aldehydes and ketones, such as, for example, menthone; isomenthone; 8-mercaptomenthan-3-one; carvone; camphor; fenchone; alpha-ionone; beta-ionone; alpha-n-methylionone; beta-n-methylionone; alpha-isomethylionone; beta-isomethylionone; alpha-irone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a-methanona-phthalen-8(5H)-one; nootkatone; dihydronootkatone; alpha-sinensal; beta-sinensal; acetylated cedarwood oil (methyl cedryl ketone);

of cyclic alcohols, such as, for example, 4-tert-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

of cycloaliphatic alcohols, such as, for example, alpha-3,3-trimethylcyclo-hexylmethanol; 2-methyl-4-(2,2,3-trimethyl-3-cyc-lopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)he-xan-3-ol;

of cyclic and cycloaliphatic ethers, such as, for example, cineol; cedryl methyl ether; cyclododecyl methyl ether; (ethoxymethoxy)cyclododecane; alpha-cedrene epoxide; 3a,6,6,9a-tetramethyidodecahydronaphtho[2,1-b]-furan; 3a-ethyl-6,6,9a-trimethyldodecahydronaphtho[2,1-b]furan; 1,5,9-trimethyl-13-oxabicyclo[10,1,0]trideca-4,8-diene; rose oxide; 2-(2,4-dimethyl-3-cyclohexen-1-yl)-5-methyl-5-(1-methylpropyl)-1,3-dioxan-e;

of cyclic ketones, such as, for example, 4-tert-butylcyclohexanone; 2,2,5-trimethyl-5-pentylcyclopentanone; 2-heptylcyclopentanone; 2-pentylcyclo-pentanone; 2-hydroxy-3-methyl-2-cyclopenten-1-one; 3-methyl-cis-2-penten-1-yl-2-cyclopenten-1-one; 3-methyl-2-pentyl-2-cycl-openten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcycl-ohexanone; 4-tert-pentylcyclohexanone; 5-cyclo-hexadecen-1-one; 6,7-dihydro-1,1,2,3,3-pentamethyl-4(5H)-indanone; 5-cyclohexadecen-1-one; 8-cyclohexadecen-1-one; 9-cycloheptadecen-1-one; cyclopentadecanone;

of cycloaliphatic aldehydes, such as, for example, 2,4-dimethyl-3-cyclo-hexenecarbal.dehyde; 2-methyl-4-(2,2,6-trimethyl-cyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

of cycloaliphatic ketones, such as, for example, 1-(3,3-dimethylcyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naph-thalenyl methyl ketone; methyl-2,6,10-trimethyl-2,5,9-cyclododecatrienyl ketone; tert-butyl 2,4-dimethyl-3-cyclohexen-1-yl ketone;

of esters of cyclic alcohols, such as, for example, 2-tert-butylcyclohexyl acetate; 4-tert-butylcyclohexyl acetate; 2-tert-pentylcyclohexyl acetate; 4-tert-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

of esters of cycloaliphatic carboxylic acids, such as, for example, allyl 3-cyclohexyl-propionate; allyl cyclohexyloxyacetate; methyl dihydro-jasmonate; methyl jasmonate; methyl 2-hexyl-3-oxocyclopentane-car-boxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolan-2-acetate;

of aromatic hydrocarbons, such as, for example, styrene and diphenylmethane;

of araliphatic alcohols, such as, for example, benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-methyl-3-phenylpropano-1; 2-methyl-5-phenylpentanol; 3-methyl-5-phenylpentanol; 3-phenyl-2-propen-1-ol; 4-methoxybenzyl alcohol; 1-(4-isopropylphenyl)eth-anol;

of esters of araliphatic alcohols and aliphatic carboxylic acids, such as, for example, benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate; of araliphatic ethers, such as, for example, 2-phenylethyl methyl ether; 2-phenylethyl isoamyl ether; 2-phenylethyl 1-ethoxyethyl ether; phenylacetaldehyde dimethyl acetal; phenylacetaldehyde diethyl acetal; hydratropaldehyde dimethyl acetal; phenylacetaldehyde glycerol acetal; 2,4,6-trimethyl-4-phenyl-1,3-dioxane; 4,4a,5,9b-tetrahydroindeno-[1,2-d]-m-dioxin; 4,4a, 5,9b-tetrahydro-2,4-dimethylindeno[1,2-d]-m-dioxin-;

of aromatic and araliphatic aldehydes, such as, for example, benzaldehyde; phenylacetaldehyde; 3-phenylpropanal; hydratropaldehyde; 4-methyl benzaldehyde; 4-methyl phenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxy-benzaldehyde; 4-hydroxy-3-methoxybenzaldehyde; 4-hydroxy-3-ethoxy-benzaldehyde; 3,4-methylenedioxybenzaldehyde; 3,4-dimethoxy-benzaldehyde; 2-methyl-3-(4-methoxyphenyl)propanal; 2-methyl-3-(4-methylendioxyphenyl)propanal;

of aromatic and araliphatic ketones, such as, for example, acetophenone; 4-methylacetophenone; 4-methoxyacetophenone; 4-tert-butyl -2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methylet-hyl)-1H-5-indenyl]ethanone; 5', 6', 7', 8'-tetrahydro-3', 5', 5', 6', 8', 8'-hexamethyl-2-acetonaphthone;

of aromatic and araliphatic carboxylic acids and esters thereof, such as, for example, benzoic acid; phenylacetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnamate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy -3,6-dimethylbenzoate; ethyl 3-phenylglycidate; ethyl 3-methyl -3-phenylglycidate;

of nitrogen-containing aromatic compounds, such as, for example, 2,4,6-trinitro-1,3-dimethyl-5-tert-butyl benzene; 3,5-dinitro-2,6-dimethy-1-4-tert-butylacetophenone; cinnamonitrile; 5-phenyl-3-methyl-2-pentenenitrile; 5-phenyl-3-methylpentanenitrile; methyl anthranilate; methyl N-methylanthranilate; Schiff bases of methyl anthranilate with 7-hydroxy-3,7-dimethyloctanal; 2-methyl-3-(4-tert-butylphenyl)propanal or 2,4-dimethyl -3-cyclohexenecarbaldehyde; 6-isopropylquinoline; 6-isobutylquinoline; 6-sec-butylquinoline; indole; skatole; 2-methoxy-3-isopropylpyrazine; 2-isobutyl-3-methoxypyrazine;

of phenols, phenyl ethers and phenyl esters, such as, for example, estragole; anethole; eugenole; eugenyl methyl ether; isoeugenole; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenylacetate;

of heterocyclic compounds, such as, for example, 2,5-dimethyl-4-hydroxy-2H-furan-3-one; 2-ethyl-4-hydroxy-5-methyl-2H-furan-3-one; 3-hydroxy -2-methyl-4H-pyran-4-one; 2-ethyl-3-hydroxy-4H-pyran-4-one;

of lactones, such as, for example, 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentade-canolide; cis- and trans-11-pentadecen-1,1-5-olide; cis- and trans -12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; coumarin; 2,3-dihydrocoumarin; octahydrocoumarin.

Fragrances or perfume oils, which contain the depot preparation according to the present invention, can be used in liquid form, undiluted or diluted with a solvent for perfuming. Suitable solvents include, for example, ethanol, isopropanol, diethylene glycol monoethyl ether, glycerol, propylene glycol, 1,2-butylene glycol, dipropylene glycol, diethyl phthalate, triethyl citrate, isopropyl myristate etc.

In addition, fragrances or perfume oils, which contain the depot preparation according to the present invention, can be adsorbed to a carrier substance which serves both to distribute fragrances finely within the product and to release them in a controlled manner during use. Such carriers may be porous in organic materials, such as light sulphate, silica gels, zeolites, gypsums, clays, clay granules, gas concrete etc., or organic materials such as wood and cellulose-based substances.

Fragrances or perfume oils, which contain the depot preparation according to the present invention, can also be microencapsulated, spray-dried, in the form of inclusion complexes or in the form of extrusion products and can be added in this form to the product to be perfumed.

The properties of the fragrances or perfume oils modified in this way can optionally be "coated" with suitable materials for a more targeted scent release, preferably the oils can be coated with wax-like synthetic materials, such as, for example, polyvinyl alcohol.

The microencapsulation of the fragrances or perfume oils can, for example, be carried out by the "coacervation process" using capsule materials made from, for example, polyurethane-like substances or soft gelatines. The spray-dried perfume oils can, for example, be prepared by spray drying an emulsion or dispersion comprising the perfume oil, where the carriers used can be modified starches, proteins, dextrin and vegetable gums. Inclusion complexes can be prepared, for example, by introducing dispersions of the perfume oil and cyclodextrins or urea derivatives into a suitable solvent, e.g. water. Extrusion products can be obtained by melting the perfume oils with a suitable wax-like substance and by extrusion with subsequent solidification, optionally in a suitable solvent, e.g. isopropanol.

In perfume compositions the amount of depot preparation, according to the present invention, used is 0.01 to 75% by weight, preferably 0.05 to 50% by weight, more preferably 0.5 to 20% by weight, based on the overall perfume oil.

Fragrances or perfume oils, which comprise the depot preparation according to the present invention, can be used in concentrated form, in solutions or in above-described modified form for the preparation of, for example, cosmetic care products. This is true particularly for washing products or other product applications where a long-lasting odor impression on the skin or the hair is desired. Examples which may be mentioned include: perfume extracts, eu de perfumes, eu de toilettes, aftershaves, ex de Colognes, preshave products, splash colognes, body care compositions such as, for example, solid and liquid soaps, shower gels, shampoos, shaving soaps, shaving foams, bath oils, cosmetic emulsions of the oil-in-water type, the water-in-oil type and the water-in-oil-in-water type, such as, for example, skin creams and lotions, face creams and lotions, sunscreen creams and lotions, aftersun creams and lotions, hand creams and lotions, foot creams and lotions, depilatory creams and lotions, aftershave creams and lotions, tanning creams and lotions, hair care products such as, for example, hairsprays, hair gels, setting hair lotions, hair rinses, permanent and semi-permanent hair colorants, hair shaping compositions, such as cold waves and hair-smoothing compositions, hair tonics, hair creams and lotions, deodorants and antiperspirants, such as, for example, underarm sprays, roll-ons, deodorant sticks, deodorant creams, products for decorative cosmetics, such as, for example, eyeshadows, nail varnishes, make-up, lipsticks, mascara.

Fragrances or perfume oils which contain the depot preparation according to the present invention can preferably be used in concentrated form, in solutions or in the above-described modified form for the preparation of hair care products, deodorants and antiperspirants and here in particular for the preparation of permanent hair colorants.

In addition, fragrances or perfume oils, which contain the depot preparation according to the present invention, can be used in concentrated form, in solutions or in the above-described modified form for the preparation of, for example, household products, such as floor cleaners, window cleaners, dishwashing detergents, bath and sanitary cleaners, scouring milk, solid and liquid WC cleaners, pulverulent and foam carpet cleaners, liquid laundry detergents, pulverulent laundry detergents, laundry pretreatment agents such as bleaches, soaking agents and stain removers, fabric softeners, washing soaps, washing tablets, disinfectants, surface disinfectants.

Preferably, fragrances or perfume oils, which contain the depot preparation according to the present invention, can be used in concentrated form, in solutions or in the above-described modified form for the preparation of liquid or pulverulent laundry detergents.

Moreover, the depot preparation according to the present invention can be used for the aromatization of, for example, packing products or foods, and use forms thereof for the use as food for human or animal consumption.

Preferred products to be aromatized include, for example, confectionery, bakery goods, chocolates, gelatin goods, sweets, alcoholic beverages, nonalcoholic beverages, ice cream, yogurt, milk drinks, soups, sauces, snacks, chewing gum, mouthwash, meat and sausage goods, vegetable protein goods, fish, cheese and baby food.

The acylals of the formula (I), according to the present invention, in which $R^2=R^3$ and which have the above-mentioned meaning can be prepared by the methods well known to the person skilled in the art (T. W. Greene, P. G. M. Wuts, Protective Groups in Organic Synthesis, 2nd Edition, John Wiley & Sons, Inc., New York 1991). Typically, the aldehyde is reacted with a carboxylic anhydride in the presence of catalytic amounts of acid. Acids which can be used for the reaction include: sulfuric acid, iron chloride, phosphorous trichloride and acidic ion exchangers. Further compounds which catalyze the acylal formation include: N-bromo-succinimide (Karimi, B.; Seradj, H.; Ebrahimian, G. R., Synlett, 623-624, 2000), copper triflate (Chandra, K. L.; Saravanan, P.; Singh, V. K., Synlett, 359-360, 2000), boron trifluoride (Sydnes, L. K.; Sandberg, M., Tetrahedron, 53, 12679-12690, 1997), LiBr (Kumar, H. M. S.; Reddy, B. V. S.; Reddy, P. T.; Yadav, J. S., J. Chem. Res. (S), 86-87, 2000) $TiO_2/SO_4^{2-}$-super acid (Jin, T.-S.; Ma, Y.-R.; Sun, X.; Liang, D.; Li, T.-S., J. Chem. Res. (S), 96-97, 2000). Preferred acids are iron chloride and sulfuric acid.

For the preparation of the acylals of the general formula (I), according to the present invention, in which $R^2 \neq R^3$ and which also have the above-mentioned meaning, the aldehyde can be reacted with a 1:1 mixture of two carboxylic anhydrides in the presence of catalytic amounts of acid. Acids, which can be used for the reaction, include those described in the paragraph above. The resulting reaction mixture can be separated very simply by distillation or chromatography.

The following nonlimiting examples illustrate the present invention.

EXAMPLES

General procedure for the preparation of the symmetrical acylals ($R^2=R^3$):15 mmol of $FeCl_3$ are introduced into 1.0 mol of carboxylic anhydride and then 0.5 mol of aldehyde, dissolved in 0.5 mol of carboxylic anhydride, is added dropwise such that the temperature does not exceed 30.degree. C. When the reaction is complete, the reaction solution is poured onto 360 ml of cyclohexane/water (5:1), the phases are separated and the organic phase is washed until neutral with saturated $NaHCO_3$ solution. The organic phase is then dried with $Na_2SO_4$, filtered off and freed from solvent. The crude product is purified by means of distillation.

Example 1

(2,4-Dimethyl-3-cyclohexen-1-yl)(propionyloxy) methyl propionate $^1$H-NMR (200 MHz, $CDCl_3$): δ (ppm)=0.89 (d, J=7.0 Hz, 3H), 1.14 (t, J=7.5 Hz, 6H), 1.47-1.55 (m, 2H), 1.63-1.67

(m, 3H), 1.86-2.07 (m, 4H), 2.35 (q, J=7.5 Hz, 4H), 5.31-5.37 (m, 1H), 6.8 (d, J=8.1 Hz, 1H).

$^{13}$C-NMR (50 MHz, CDCl$_3$): δ (ppm)=8.9, 15.6, 18.6, 20.7, 23.3, 27.4, 27.5, 29.7, 30.1, 40.7, 91.3, 126.8, 132.8, 172.4, 172.5.

Example 2

(Butyryloxy) (2,4-dimethyl-3-cyclohexen-1-yl)methyl butyrate $^1$H-NMR (200 MHz, CDCl$_3$): δ (ppm)=0.89 (d, J=7.0 Hz, 3H), 0.95 (t, J=7.5 Hz, 6H), 1.47-1.55 (m, 2H), 1.62-1.71 (m, 7H), 1.86-2.06 (m, 4H), 2.28-2.33 (m, 4H), 5.31-5.37 (m, 1H), 6.8 (d, J=8.1 Hz, 1H).

$^{13}$C-NMR (50 MHz, CDCl$_3$): δ (ppm)=13.5 (2C), 13.6, 15.6, 18.2, 18.6, 23.3, 29.7, 30.1, 36.0, 36.1, 40.6, 91.2, 126.7, 132.8, 171.6, 171.7.

Example 3

(Butyryloxy) [4-(4-methyl-3-pentenyl)-3-cyclohexen-1-yl]methyl butyrate $^1$H-NMR (200 MHz, CDCl$_3$): δ (ppm)=0.95 (t, J=7.3 Hz, 6H), 1.60 (s, 3H), 1.61-1.68 (m, 4H), 1.69 (s, 3H), 1.76-1.84 (m, 1H), 1.88-2.10 (m, 10H), 2.28-2.34 (m, 4H), 5.09 (tq, J=6.8, 1.3 Hz, 1H), 5.35-5.43 (m, 1H), 6.75 (d, J=5.4 Hz, 1H).

$^{13}$C-NMR (50 MHz, CDCl$_3$): δ (ppm)=13.6 (2C), 17.6, 18.3 (2C), 23.4, 25.6, 25.7, 26.4, 27.8, 36.0 (2C), 37.3, 37.6, 91.9, 118.8, 124.2, 131.4, 137.7, 171.7, 171.8.

Example 4

[4-(4-Methyl-3-pentenyl)-3-cyclohexen-1-yl](propionyloxy)methyl propionate $^1$H-NMR (200 MHz, CDCl$_3$): δ (ppm)=1.15 (t, J=7.5 Hz, 6H), 1.60 (s, 3H), 1.68 (s, 3H), 1.75-1.84 (m, 1H), 1.89-2.10 (m, 10H), 2.30-2.42 (m, 4H), 5.09 (tq, J=6.8, 1.3 Hz, 1H), 5.35-5.43 (m, 1H), 6.75 (d, J=5.4 Hz, 1H).

$^{13}$C-NMR (50 MHz, CDCl$_3$): δ (ppm)=8.8 (2C), 23.3, 25.6, 25.7 (2C), 26.4, 27.4 (2C), 27.8, 37.3, 37.5, 91.9, 118.8, 124.2, 131.5, 137.7, 172.6, 172.7.

Example 5

(Butyryloxy)(phenyl)methyl butyrate $^1$H-NMR (200 MHz, CDCl$_3$): δ (ppm)=0.95 (t, J=7.4 Hz, 6H), 1.67 (sex, J=7.4 Hz, 4H), 2.32-2.40 (m, 4H), 7.37-7.44 (m, 3H), 7.48-7.55 (m, 2H), 7.71 (s, 1H).

$^{13}$C-NMR (50 MHz, CDCl$_3$): δ (ppm)=13.5 (2C), 18.2 (2C), 35.9 (2C), 89.4, 126.5 (2C), 128.5 (2C), 129.5, 135.7, 171.3 (2C).

Example 6

3-(4-tert-Butylphenyl)-1-(butyryloxy)propyl butyrate $^1$H-NMR (200 MHz, CDCl$_3$): δ (ppm)=0.95 (t, J=7.2 Hz, 6H), 1.30 (s, 9H), 1.65 (sex, J=7.2 Hz, 4H), 2.04-2.16 (m, 2H), 2.24-2.33 (m, 4H), 2.63-2.74 (m, 2H), 6.87 (t, J=5.5 Hz, 1H), 7.12 (d, J=8.0 Hz, 2H), 7.31 (d, J=8.0 Hz, 2H).

$^{13}$C-NMR (50 MHz, CDCl$_3$): δ (ppm)=13.5 (2C), 18.1 (2C), 29.1, 31.3 (3C), 34.3, 34.6, 35.8 (2C), 89.8, 125.2 (2C), 127.8 (2C), 137.3, 148.7, 171.4 (2C).

Example 7

1-(Heptanoyloxy)decyl heptanoate $^1$H-NMR (200 MHz, CDCl$_3$): δ (ppm)=0.83-0.93 (m, 9H), 1.22-1.38 (m, 28H), 1.53-1.77 (m, 4H), 2.31, (t, J=7.4 Hz, 4H), 6.79 (t, J=5.6 Hz, 1H)

$^{13}$C-NMR (50 MHz, CDCl$_3$): δ (ppm)=14.0 (2C), 14.1, 22.4 (2C), 22.6, 23.4, 24.6 (2C), 28.6 (2C), 29.1, 29.2, 29.4 (2C), 31.4 (2C), 31.8, 33.2, 34.1 (2C), 90.2, 171.7 (2C).

Example 8

1-(Acetyloxy)heptyl acetate $^1$H-NMR (200 MHz, CDCl$_3$): δ (ppm)=0.88 (t, J=6.5 Hz, 3H), 1.23-1.42 (m, 8H), 1.70-1.82 (m, 2H), 2.08 (s, 6H), 6.77 (t, J=5.6 Hz, 1H). $^{13}$C-NMR (50 MHz, CDCl$_3$): δ (ppm)=14.0, 20.8 (2C), 22.5, 23.3, 28.8, 31.6, 33.1, 90.4, 168.9 (2C).

Example 9

(Acetyloxy)(2,4-dimethyl-3-cyclohexen-1-yl)methyl acetate Isomerism data: cis/trans=2.3:1.

$^1$H-NMR (200 MHz, CDCl$_3$): δ (ppm)=0.88 (d, J=7.0 Hz, 3H), 1.43-1.57 (m, 2H), 1.62-1.67 (m, 3H), 1.90-2.04 (m, 3H), 2.08 (s, 6H), 2.26-2.40 (m, 1H), 5.30-5.37 (m, 1H), 6.77 (d, J=8.2 Hz, 1H).

$^{13}$C-NMR (50 MHz, CDCl$_3$): δ (ppm)=15.5, 18.5, 20.8 (2C), 23.3, 29.6, 30.1, 40.5, 91.3, 126.5, 132.6, 168.9 (2C).

Example 10

1-(Acetyloxy)-2-methylundecyl acetate $^1$H-NMR (200 MHz, CDCl$_3$): δ (ppm)=0.88 (t, J=6.3 Hz, 3H), 0.95 (d, J=6.7 Hz, 3H), 1.20-1.32 (m, 16H), 1.77-1.93 (m, 1H), 2.08 (s, 6H), 6.69 (d, J=4.4 Hz, 1H).

$^{13}$C-NMR (50 MHz, CDCl$_3$): δ (ppm)=13.3, 14.1, 20.7, 20.8, 22.7, 26.8, 29.3, 29.5, 29.6, 29.7, 30.8, 31.9, 36.3, 92.3, 168.9 (2C).

General procedure for the preparation of asymmetrical acylals (R$^2$≠R$^3$) 15 mmol of FeCl$_3$ are introduced into 1.0 mol of a 1:1 mixture of two carboxylic anhydrides and then 0.5 mol of aldehyde, dissolved in 0.5 mol of a 1:1 mixture of two carboxylic anhydrides, is then added dropwise so that the temperature does not exceed 30.degree. C. When the reaction is complete, the reaction solution is poured onto 360 ml of cyclohexane/water (5:1), the phases are separated and the organic phase is washed until neutral with saturated NaHCO$_3$ solution. The organic phase is then dried with Na$_2$SO$_4$, filtered off and freed from solvent. The product mixture is purified by means of distillation or chromatography.

Example 11

1-(Acetyloxy)-3-(4-tert-butylphenyl)propyl hexanoate $^1$H-NMR (200 MHz, CDCl$_3$): δ (ppm)=0.90 (t, J=7.3 Hz, 3H), 1.30 (s, 9H), 1.24-1.39 (m, 4H), 1.51-1.75 (m, 2H), 2.05 (s, 3H), 2.04-2.16 (m, 2H), 2.26-2.37 (m, 2H), 2.63-2.74 (m, 2H), 6.85 (t, J=5.4 Hz, 1H), 7.12 (d, J=8.1 Hz, 2H), 7.31 (d, J=8.1 Hz, 2H).
$^{13}$C-NMR (50 MHz, CDCl$_3$): δ (ppm)=13.9, 20.7, 22.3, 24.3, 29.0, 31.1, 31.3 (3C), 33.9, 34.3, 34.6, 89.9, 125.2 (2C), 127.8 (2C), 137.3, 148.7, 168.8, 171.6.

Example 12

1-(Acetyloxy)-3-(4-tert-butylphenyl)propyl heptanoate $^1$H-NMR (200 MHz, CDCl$_3$): δ (ppm)=0.88 (t, J=7.1 Hz, 3H), 1.30 (s, 9H), 1.24-1.38 (m, 6H), 1.52-1.71 (m, 2H), 2.05 (s, 3H), 2.03-2.18 (m, 2H), 2.26-2.38 (m, 2H), 2.63-2.74 (m, 2H), 6.85 (t, J=5.4 Hz, 1H), 7.12 (d, J=8.0 Hz, 2H), 7.31 (d, J=8.0 Hz, 2H).
$^{13}$C-NMR (50 MHz, CDCl$_3$): δ (ppm)=14.0, 20.7, 22.4, 24.5, 28.6, 29.0, 31.3 (3C), 31.4, 33.9, 34.3, 34.6, 89.9, 125.2 (2C), 127.8 (2C), 137.3, 148.7, 168.7, 171.6.

Example 13

1-(Acetyloxy)decyl hexanoate $^1$H-NMR (200 MHz, CDCl$_3$): δ (ppm)=0.84-0.96 (m, 6H), 1.22-1.40 (m, 18H), 1.55-1.82 (m, 4H), 2.07 (s, 3H), 2.44 (t, J=7.4 Hz, 2H), 6.78 (t, J=5.6 Hz, 1H).
$^{13}$C-NMR (50 MHz, CDCl$_3$): δ (ppm)=13.9, 14.1, 20.8, 22.3, 22.7, 23.4, 24.3, 29.1, 29.3, 29.4 (2C), 31.1, 31.9, 33.2, 34.0, 90.4, 168.9, 171.7.

Example 14

1-(Acetyloxy)decyl heptanoate $^1$H-NMR (200 MHz, CDCl$_3$): δ (ppm)=0.83-0.95 (m, 6H), 1.22-1.40 (m, 20H), 1.54-1.82 (m, 4H), 2.07 (s, 3H), 2.45 (t, J=7.4 Hz, 2H), 6.78 (t, J=5.6 Hz, 1H).
$^{13}$C-NMR (50 MHz, CDCl$_3$): δ (ppm)=14.0, 14.1, 20.8, 22.5, 22.7, 23.4, 24.6, 28.6, 29.1, 29.3, 29.5 (2C), 31.4, 31.9, 33.2, 34.1, 90.4, 168.9, 171.7.

The depot preparations according to the present invention were incorporated into numerous consumer products and their performance properties were investigated using various methods. For the preparation of the formulations for the consumer products, molar equivalents of the aldehydes were used in the form of the acylals or in the form of the free aldehydes in order to ensure comparability.

Method 1: Storage Stability

The storage stability of a fragrance or of a depot preparation is defined by the percentage of substance still present after storage.

(Amount after storage/Amount before storage)
*100%=Storage stability [%]

For the determination and for the comparison of the storage stability the depot preparation (DP) consisting of one or more acylals and the corresponding aldehydes (AL) are incorporated into separate samples. (S.sub.DP and S.sub.AL) of the same formulation of a consumer product, such as, for example, laundry detergent, shampoo or soap. The separate samples are then divided into portions. One portion of the sample S.sub.DP and S.sub.AL is subjected immediately to a suitable extraction and analytical measurement in order to determine the amount of depot preparation or aldehyde prior to storage. In the analytical investigation by, for example, gas chromatography, a suitable standard is used for quantification. The second portion is subjected to storage at elevated temperature for a defined period and then extracted and quantified using the same methods.

Method 2: Odor Evaluation

The odor evaluation of a depot preparation per se or in comparison with the corresponding aldehydes is carried out by a group of trained individuals. Here, the odor strength of the consumer product in use with regard to the aldehyde used is assessed. The consumer product is used according to its designation for application to the skin or for the washing of laundry, skin or hair. During use, the consumer product itself, its aqueous solutions, the damp or dry laundry or the damp or dry skin, for example, is then assessed in terms of odor on a scale from 1 (weak odor) to 6 (strong odor).

Method 3: Headspace Release Rate

The analytical measurement of the concentration of fragrances themselves, the depot preparations and the fragrances released from the depot preparations is carried out by means of gas chromatography. In this connection, various injection methods, such as, for example, thermo-desorption, liquid injection and gas injection, can also be used.

Prior to the analytical measurement of fragrances, various enrichment methods, such as, for example, extraction, concentration or adsorption, can be used. Suitable extractants for liquid-liquid or liquid-solid extractions include, for example, solvents such as, for example, carbon dioxide, ethers, ketones, hydrocarbons, alcohols, water and esters.

In addition, by freezing a static or dynamic headspace above the perfumed product or substrates treated with the perfumed product, such as hair, textiles or skin, by means of cool traps, an enrichment or concentration can be achieved.

For the adsorption or extraction of fragrances from a static or dynamic headspace, surface-active adsorbents such as, for example, hair, textiles, ceramic, plastic, activated carbon and also poly-2,6-diphenyl-p-phenylene oxide (Tenax®) and crosslinked porous polymers based on styrene, ethylvinylbenzene, vinylpyrrolidone, vinylpyrridine and ethylene glycol dimethacrylate (Poropax® series), are suitable. The fragrances enriched on these adsorbents are then desorbed by heating (thermo-desorption) or using solvents and can then be analyzed.

Example 15

Powder Laundry Detergents

The laundry detergents A and B were used for washing or examined analytically both directly and after storage for four weeks.

TABLE 1

Powder laundry detergent formulation

| Ingredients | | A | B |
| --- | --- | --- | --- |
| Powder laundry detergent | | 99.7 | 99.84 |
| DP Example 3 (4) | (Butyryloxy)[4-(4-methyl-3-pentenyl)-3-cyclohexen-1-yl]methyl butyrate | 0.3 | |
| Vertomugal (4) | 1-Formyl-4-(4-methyl-3-pentenyl)-3-cyclohexen | | 0.16 |

1-Formyl-4-(4-methyl-3-pentenyl)-3-cyclohexene

Odor Assessment

Cotton fabric and synthetic fabric were washed together in two different machines at the same time with the above-mentioned laundry detergents A and B and evaluated in terms of odor in the damp and in the dry state: the odor strength of the items of laundry which were washed with the laundry detergent A containing depot preparation was significantly higher than the odor strength of the items of laundry which were washed with the laundry detergent B containing the free aldehyde.

Storage Stability

The storage stability of the free aldehyde after one month was 34%. The acid formed from the free aldehyde produced an unpleasant odor note. The storage stability of the aldehyde in the depot preparation was 93% and was thus significantly higher.

Release Rate

The washed textiles A and B were each transferred to separate glass bottles. SPME analysis ("Solid Phase Microextraction") or direct headspace analysis was then used to analyze the relative concentration of free aldehyde. More than five times more free aldehyde was found in the headspace above the damp laundry washed with the laundry detergent A. Seven times more aldehyde was found in the headspace above the dry laundry washed with the laundry detergent A.

Example 16

Soap

The soap formulation below can be prepared in accordance with generally known methods. The data refer to percentages by weight. The resulting soaps A to F were used for washing or examined analytically both directly and also after storage for four weeks.

TABLE 2

| Soap formulation | | | | | | | |
|---|---|---|---|---|---|---|---|
| Ingredients | | A | B | C | D | E | F |
| Soap base (1) | Sodium Tallowate | 75.0 | 75.0 | 75.0 | 75.0 | 75.0 | 75.0 |
| Soap base (1) | Sodium Cocoate | 10.0 | 10.0 | 10.0 | 10.0 | 10.0 | 10.0 |
| Water | Water | 13.0 | 13.0 | 13.0 | 13.0 | 13.0 | 13.0 |
| Bayertitan AZ (2) | Titanium Dioxide | 0.3 | 0.3 | 0.3 | 0.3 | 0.3 | 0.3 |
| Tinopal CBS-X (3) | Disodium Distyrylbiphenyl Disulphonate | 0.2 | 0.2 | 0.2 | 0.2 | 0.2 | 0.2 |
| DP Example 7 (4) | 1-(Heptanoyloxy)decyl heptanoate | 0.3 | | | | | |
| Aldehyde C10 (4) | Decanal | | 0.12 | | | | |
| DP Example 5 (4) | (Butyryloxy)(phenyl) methyl butyrate | | | 0.3 | | | |
| Benzaldehyde (4) | Benzaldehyde | | | | 0.12 | | |
| DP Example 6 (4) | 3-(4-tert-Butylphenyl)-1-(buty-ryloxy)propyl butyrate | | | | | 0.3 | |
| Bourgeonal (5) | 4-tert-butyldihydrocinnamal dehyde | | | | | | 0.16 |

Suppliers
(1) Enzian Seifenfabrik, 72555 Metzingen, Germany
(2) Bayer AG, Bayerwerk, D-51368 Leverkusen, Germany
(3) Ciba Spezialittenchemie AG, 4000 Basle, Switzerland
(4) Haarmann & Reimer GmbH, D-37603 Holzminden, Germany
(5) Quest International, Ashford, England Odor and Color Assessment The soap formulations A to F were stored for about three months at room temperature.

Soaps A, C and E which contain the depot preparations showed no or only a slight color change while soaps D and F had a yellowish or grey coloration, respectively. Color stability is achieved as a result of the use of the depot preparations.

After storage, 1 g of each of the soaps was dissolved in 100 g of hand-hot water, and the bars of soaps were used for washing skin.

In all cases the scent impression above the aqueous solutions in soaps A, C and E which comprise the depot preparations was significantly stronger than the scent impression of soaps B, D and F which comprise the free aldehydes.

The scent impression of the washed skin which was washed with soaps A, C and E was likewise greater and longer lasting than the scent impression after washing with soaps B, D and F.

Storage Stability

The soap formulations A to F were stored in the dark for about one-month at room temperature. All depot preparations exhibited a significantly greater storage stability than the corresponding aldehydes.

TABLE 3

| Storage stability of depot preparations and free aldehydes in | | |
|---|---|---|
| Ingredients | | Storage stability [%] |
| DP Example 7 (4) | 1-(Heptanoyloxy)decyl heptanoate | 95 |
| Aldehyde C10 (4) | Decanal | 32 |
| DP Example 5 (4) | (Butyryloxy)(phenyl)methyl butyrate | 93 |
| Benzaldehyde (4) | Benzaldehyde | 45 |
| DP Example 6 (4) | 3-(4-tert-Butylphenyl)-1-(butyryloxy)propyl butyrate | 93 |
| Bourgeonal (5) | 4-tert-Butyldihydro-cinnamaldehyde | 27 |

Release Rate

To determine the hydrolysis rate, the depot preparation was added to a 1% strength aqueous soap solution, and the concentration of the depot preparation or of the free aldehyde was measured by SPME headspace analysis.

The depot preparations in soaps A, C and E exhibited spontaneous hydrolysis relative to the corresponding aldehydes. After just 5 minutes the depot preparation had completely hydrolyzed.

Through the suitable choice of the radicals in the depot preparation, a delayed or incomplete hydrolysis can also be achieved. As a result, some of the depot preparation can then be applied to the skin in the washing process, and then, as a result of the slower cleavage of the acylals, a long-lasting scent impression on the skin can be achieved.

Example 17

Shampoo

The following shampoo formulation can be prepared by generally known methods. The data refer to percentages by weight.

TABLE 4

Shampoo formulation

| Ingredients | Composition | A | B |
|---|---|---|---|
| Plantacare PS 10 (1) | Sodium Laureth Sulfate (and) Lauryl Glycoside | 20.000 | 20.000 |
| Demineralized Water | Water (Aqua) | ad 100% | ad 100% |
| Sodium chloride | Sodium chloride | 1.400 | 1.400 |
| Citric acid 10.0% solution | Citric Acid | 1.650 | 1.650 |
| Phenonip (2) | Phenoxyethanol (and) Methyl paraben (and) Ethylparaben (and) Propylparaben (and) Butylparaben | 0.500 | 0.500 |
| DP Example 7 (4) | 1-(Heptanoyloxy)decyl heptanoate | 0.3 | |
| Aldehyde C10 (4) | Decanal | | 0.12 |

Odor Assessment

The resulting shampoos A and B were used for washing hair tresses or in a half-head washing test on test persons. In the half-head washing test, one half of the hair of the test persons was in each case washed with shampoo A, and the other half of the hair was washed with shampoo B.

The hair tresses washed with shampoo B had a slightly higher odor strength after washing compared with the hair tresses which were washed with shampoo A. However, the odor intensity of the hair washed with shampoo B decreased rapidly and was no longer distinguishable from a neutral sample after about four hours.

The same scent evaluation was also obtained for the half-head washing test on test persons. However, a long-lasting aldehyde odor was perceived from the half which was washed with shampoo A. Even after a few days a significant aldehyde odor was perceivable on the hair half A. As a result of the greater transfer and subsequent slow cleavage of the depot preparation relative to the free aldehyde, a long-lasting scent impression can be achieved. This demonstrates the advantage of the depot preparation compared with the free aldehyde in the application.

Example 18

Permanent Hair Colorant

Stability in the Developer Mass

The formulation of the developer mass typically comprises water, hydrogen peroxide, acids, such as, for example, phosphoric acid, citric acid etc., thickeners, emulsifiers, preservatives, solvents and further auxiliaries. 1% of DP Example 5 is added to the formulation of the developer mass.

The developer formulation, which comprises 1% of DP Example 5, is stored for one and a half months at room temperature.

TABLE 5

Storage stability of depot preparation in developer mass

| | Stability [%] 0 days | Stability [%] 13 days | Stability [%] 28 days | Stability [%] 42 days |
|---|---|---|---|---|
| DP Example 5 (4) | 100 | 100 | 98 | 100 |

The depot preparation is color, odor and analytically stable over the period of one and half months.

Release Rate During Hair Coloring

To determine the hydrolysis rate the three depot preparations DP Example 8, DP Example 9 and DP Example 10 were added to the developer mass in a concentration of in each case 0.3%. The ammoniacal dye solution, which consists of 2 to 16% ammonia and/or substitutes such as, for example, alkanolamines, in particular monoethanolamine, water, thickeners, emulsifier, bodying agents, reactive dyes, solvents, flexing agents, stabilizers and preservatives, is then added to the developer mass in the ratio 1:1. Samples are then taken from the hair dye solution at defined time intervals, neutralized and extracted with solvent, and the content of depot preparation and released aldehyde is determined by means of gas chromatography using an internal and external standard.

TABLE 6

Release rate during hair coloring

| | Relative GC content [%] | | | | | |
|---|---|---|---|---|---|---|
| Time (min) | Aldehyde C7 | Vertocitral | 2-Methylundecanal | DP Example 8 | DP Example 9 | DP Example 10 |
| 1 | 1.4 | 2.1 | 2.8 | 22.9 | 28.9 | 48.2 |
| 5 | 17.1 | 33.6 | 32.8 | 0.0 | 2.5 | 5.1 |
| 10 | 19.3 | 33.6 | 47.1 | 0.0 | 0.5 | 2.0 |
| 20 | 12.2 | 19.3 | 20.7 | 0.0 | 0.0 | 0.0 |
| 30 | 11.4 | 15.7 | 16.4 | 0.0 | 0.0 | 0.0 |

The depot preparations in the formulation for hair coloring exhibited, after combining the developer mass with the ammoniacal hair dye solution, spontaneous hydrolysis relative to the corresponding aldehydes. After just 5 minutes the depot preparations were virtually completely hydrolyzed.

Odor Assessment

TABLE 7

Developer formulation

| Ingredients | A | B | C | D |
|---|---|---|---|---|
| Developer mass | 100% | 99.7% | 99.7% | 99.7% |
| DP Example 8 (1-(acetyloxy)heptyl acetate) | | 0.3% | | |
| DP Example 9 (acetyloxy)(2,4-dimethyl-3-cyclo-hexen-1-yl)methyl acetate) | | | 0.3% | |
| DP Example 10 (1-(acetyl-oxy)-2-methylundecyl acetate | | | | 0.3% |

The resulting developers A to D were combined with the ammoniacal dye solution in the ratio 1:1, stirred for two minutes and then applied to four hair tresses. In the case of the hair tresses, which had been coated with the developer formulations B to D, a significant aldehyde odor was perceivable directly after application. The odor impression intensified or remained constant over a period of 30 minutes.

TABLE 8

Sensory aldehyde intensity during the hair coloring process

| Time (min) | Sensory intensity | | |
|---|---|---|---|
| | Aldehyde C7 | Vertocitral | 2-Methylundecanal |
| 1 | 4.0 | 4.6 | 4.6 |
| 2 | 5.0 | 5.4 | 5.4 |
| 4 | 6.0 | 5.8 | 5.8 |
| 8 | 6.2 | 6.0 | 6.0 |
| 15 | 6.2 | 6.0 | 6.0 |
| 25 | 4.4 | 5.4 | 5.4 |

The scale for sensory intensity ranges from 1.0=odorless to 9.0=very strong.

This shows, surprisingly, a significant advantage in using the depot preparations according to the present invention for the targeted release of aldehydes in perfume oils for alkaline hair colorants.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A permanent hair coloring comprising:
an ammoniacal dye solution comprising ammonia and/or an ammonia substitute; and
a developer mass, wherein the developer mass includes at least one depot compound of the formula (I)

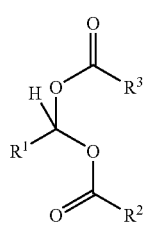

(I)

wherein $R^1$, $R^2$ and $R^3$, independently, are an organic radical having 1 to 30 carbon atoms, and wherein the compound of the formula (I) releases an aldehyde and two carboxylic acids as a result of hydrolysis or enzymatic cleavage following mixing of the ammoniacal dye solution and the developer mass, said aldehyde released by said compound of formula (I) having a molecular weight of from 100 to 350 g/mol, wherein said aldehyde released by said compound of formula (I) is selected from the group consisting of: phenylacetaldehyde, p-methylphenylacetaldehyde, p-isopropylphenylacetaldehyde, methylnonylacetaldehyde, phenylpropanal, 3-(4-t-butylphenyl)-2-methylpropanal (lilial), 3-(4-t-butylphenyl)propana-1(bourgeonal), 3-(4-methoxyphenyl)-2-methylpropanal (canthoxal), 3-(4-isopropylphenyl)-2-methylpropanal (cymal), 3-(3,4-methylenedioxyphen-yl)-2-methylpropanal (helional), 3-(4-ethylphenyl)-2,2-dimethylpropanal (floralozone), phenylbutanal, 3-methyl-5-phenylpentanal, hexanal, trans-2-hexenal, cis-hex-3-enal, heptanal, cis-4-heptenal, 2-ethyl-2-heptenal, 2,6-dimethyl-5-heptenal (melonal), octanal, 2-octenal, 3,7-dimethyloctanal, 3,7-dimethyl-2,6-octadien-3-al, 3,7-dimethyl-6-octenal (citronellal), 3,7-dimethyl-7-hydroxy-octan-1-al (hydroxycitronellal), nonanal, 6-nonenal, decanal, 2-methyldecanal, 4-decenal, 9-decenal, undecanal, 2-methyldecanal, 2-methylundecanal, 2,6,10-trimethyl-9-undecenal (adoxal), undec-10-enylaldehyde, undec-8-enanal, dodecanal, tridecanal, tetradecanal, anisaldehyde, cinnamal-dehyde, α-amylcinnamaldehyde, α-hexylcinnamaldehyde, methoxy-cinnamaldehyde, isocyclocitral, citronellyloxyacetaldehyde, cortexal-dehyde, cuminaldehyde, cyclamenaldehyde, florhydral, heliotropin, hydratropaldehyde, vanillin, ethylvanillin, benzaldehyde, p-methylbenz-aldehyde, 3,4-dimethoxybenzaldehyde, 3- and 4-(4-hydroxy-4-methyl-pentyl)-3-cycloh-exene-1-carboxaldehyde (lyral), 2,4-dimethyl-3-cyclohexene-1-carboxaldehyde (triplal), l-methyl-3-(4-methylpentyl)-3-cyclohexenecarboxaldehyde (vernaldehyde) or p-methylphenoxyacetaldehyd-e (Xi aldehyde).

2. The hair coloring according to claim 1, wherein the ammoniacal dye solution comprises 2 to 16% ammonia and/or ammonia substitute.

3. The hair coloring according to claim 2, wherein the ammonia substitute is an alkanolamine.

4. The hair coloring according to claim 1, wherein the hair coloring composition includes a fragrance or a perfume oil, and further includes, in addition to the depot compound of formula (I), natural raw materials, hydrocarbons, aliphatic alcohols, aliphatic ketones, aliphatic nitriles, aliphatic carboxylic acids, acyclic terpene alcohols, acyclic terpene aldehydes, cyclic terpene aldehydes, cyclic alcohols, cycloaliphatic alcohols, cyclic or cycloaliphatic ethers, cyclic ketones, cycloaliphatic aldehydes or ketones, esters of cyclic alcohols or carboxylic acids, aromatic hydrocarbons, araliphatic alcohols, esters of araliphatic alcohols with aliphatic carboxylic acids, aromatic or araliphatic aldehydes, ketones or carboxylic acids, nitrogen-containing, aromatic compounds, phenols, phenyl ethers or phenyl esters, heterocyclic compounds or lactones.

5. The hair coloring according to claim 4, wherein the fragrance or perfume oil is adsorbed to a carrier substance.

6. The hair coloring according to claim 4, wherein the fragrance or perfume oil is microencapsulated or spray-dried or in the form of inclusion complexes or extrusion products.

7. A process for releasing an aldehyde and two carboxylic acids, the process comprising (a) preparing a permanent hair coloring composition comprising a developer mass, wherein the developer mass includes at least one depot compound of the formula (I)

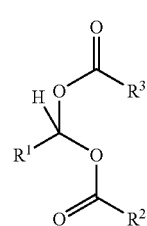

(I)

wherein $R^1$, $R^2$ and $R^3$, independently, are an organic radical having 1 to 30 carbon atoms, and (b) cleaving the depot compound of the formula (I) under the influence of at least one of ammonia or an ammonia substitute so that an aldehyde and two carboxylic acids are released, wherein said cleaving step comprises mixing said developer mass with an ammoniacal dye solution comprising the ammonia and/or an ammonia substitute.

8. A process for dying hair, comprising (a) applying to hair a permanent hair coloring composition comprising a developer mass, wherein the developer mass includes at least one depot compound of the formula (I)

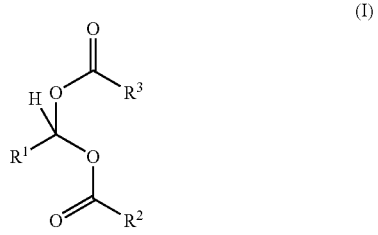

wherein $R^1$, $R^2$ and $R^3$, independently, are an organic radical having 1 to 30 carbon atoms, and (b) cleaving the depot compound of the formula (I) under the influence of at least one of ammonia or an ammonia substitute so that an aldehyde and two carboxylic acids are released, said aldehyde released by said compound of formula (I) having a molecular weight of from 100 to 350 g/mol, wherein said cleaving step comprises mixing said developer mass with an ammoniacal dye solution comprising the ammonia and/or an ammonia substitute.

9. The process as in claim 8, wherein in the formula (I) $R^1$ is a saturated or unsaturated, linear or branched, alicyclic or aromatic radical having 1 to 18 carbon atoms, and $R^2$ and $R^3$, independently of one another, are a saturated or unsaturated, linear or branched, alicyclic or aromatic radicals having 1 to 22 carbon atoms, or in which $R^2$ and $R^3$ together form a saturated or unsaturated, branched or unbranched carbocyclic or aromatic ring of 3 to 10 carbon atoms.

10. The permanent hair coloring of claim 1, wherein in the formula (I) $R^1$ is a saturated or unsaturated, linear or branched, alicyclic or aromatic radical having 1 to 18 carbon atoms, and $R^2$ and $R^3$, independently of one another, are a saturated or unsaturated, linear or branched, alicyclic or aromatic radical having 1 to 22 carbon atoms, or in which $R^2$ and $R^3$ together form a saturated or unsaturated, branched or unbranched carbocyclic or aromatic ring of 3 to 10 carbon atoms.

11. The permanent hair coloring of claim 1, wherein said aldehyde released by said compound of formula (I) has a molecular weight of from 120 to 270 g/mol.

12. The process of claim 7, wherein in the formula (I) $R^1$ is a saturated or unsaturated, linear or branched, alicyclic or aromatic radical having 1 to 18 carbon atoms, and $R^2$ and $R^3$, independently of one another, are a saturated or unsaturated, linear or branched, alicyclic or aromatic radicals having 1 to 22 carbon atoms, or in which $R^2$ and $R^3$ together form a saturated or unsaturated, branched or unbranched carbocyclic or aromatic ring of 3 to 10 carbon atoms.

13. The method of claim 7, wherein said aldehyde released by said compound of formula (I) has a molecular weight of from 120 to 270 g/mol.

14. The method of claim 7, wherein said aldehyde released by said compound of formula (I) is selected from the group consisting of: phenylacetaldehyde, p-methylphenylacetaldehyde, p-isopropyl-phenylacetaldehyde, methylnonylacetaldehyde, phenylpropanal, 3-(4-t-butylphenyl)-2-methylpropanal (lilial), 3-(4-t-butylphenyl)propana-1(bourgeonal), 3-(4-methoxyphenyl)-2-methylpropanal (canthoxal), 3-(4-isopropylphenyl)-2-methylpropanal (cymal), 3-(3,4-methylenedioxyphen-yl)-2-methylpropanal (helional), 3-(4-ethylphenyl)-2,2-dimethylpropanal (floralozone), phenylbutanal, 3-methyl-5-phenylpentanal, hexanal, trans-2-hexenal, cis-hex-3-enal, heptanal, cis-4-heptenal, 2-ethyl-2-heptenal, 2,6-dimethyl-5-heptenal (melonal), 2,4-heptadienal, octanal, 2-octenal, 3,7-dimethyloctanal, 3,7-dimethyl-2,6-octadien-1-al, 3,7-dimethyl-2,6-octadien-3-al, 3,7-dimethyl-6-octenal (citronellal), 3,7-dimethyl-7-hydroxy-octan-1-al (hydroxycitronellal), nonanal, 6-nonenal, 2,4-nonadienal, 2,6-nonadienal, decanal, 2-methyldecanal, 4-decenal, 9-decenal, 2,4-decadienal, undecanal, 2-methyldecanal, 2-methylundecanal, 2,6,10-trimethyl-9-undecenal (adoxal), undec-10-enylaldehyde, undec-8-enanal, dodecanal, tridecanal, tetradecanal, anisaldehyde, cinnamaldehyde, α-amylcinnamaldehyde, α-hexylcinnamaldehyde, methoxycinnamaldehyde, isocyclocitral, citronellyloxyacetaldehyde, cortexal-dehyde, cuminaldehyde, cyclamenaldehyde, florhydral, heliotropin, hydratropaldehyde, vanillin, ethylvanillin, benzaldehyde, p-methylbenzaldehyde, 3,4-dimethoxybenzaldehyde, 3- and 4-(4-hydroxy-4-methyl-pentyl)-3-cyclohexene-1-carboxaldehyde (lyral), 2,4-dimethyl-3-cyclohexene-1-carboxaldehyde (triplal), 1-methyl-3-(4-methylpentyl)-3-cyclohexenecarboxaldehyde (vernaldehyde) or p-methylphenoxyacetaldehyd-e (Xi aldehyde).

15. The method of claim 8, wherein said aldehyde released by said compound of formula (I) has a molecular weight of from 120 to 270 g/mol.

16. The method of claim 8, wherein said aldehyde released by said compound of formula (I) is selected from the group consisting of: phenylacetaldehyde, p-methylphenylacetaldehyde, p-isopropyl-phenylacetaldehyde, methylnonylacetaldehyde, phenylpropanal, 3-(4-t-butylphenyl)-2-methylpropanal (lilial), 3-(4-t-butylphenyl)propana-1(bourgeonal), 3-(4-methoxyphenyl)-2-methylpropanal (canthoxal), 3-(4-isopropylphenyl)-2-methylpropanal (cymal), 3-(3,4-methylenedioxyphen-yl)-2-methylpropanal (helional), 3-(4-ethylphenyl)-2,2-dimethylpropanal (floralozone), phenylbutanal, 3-methyl-5-phenylpentanal, hexanal, trans-2-hexenal, cis-hex-3-enal, heptanal, cis-4-heptenal, 2-ethyl-2-heptenal, 2,6-dimethyl-5-heptenal (melonal), 2,4-heptadienal, octanal, 2-octenal, 3,7-dimethyloctanal, 3,7-dimethyl-2,6-octadien-1-al, 3,7-dimethyl-2,6-octadien-3-al, 3,7-dimethyl-6-octenal (citronellal), 3,7-dimethyl-7-hydroxy-octan-1-al (hydroxycitronellal), nonanal, 6-nonenal, 2,4-nonadienal, 2,6-nonadienal, decanal, 2-methyldecanal, 4-decenal, 9-decenal, 2,4-decadienal, undecanal, 2-methyldecanal, 2-methylundecanal, 2,6,10-trimethyl-9-undecenal (adoxal), undec-10-enylaldehyde, undec-8-enanal, dodecanal, tridecanal, tetradecanal, anisaldehyde, cinnamaldehyde, α-amylcinnamaldehyde, α-hexylcinnamaldehyde, methoxycinnamaldehyde, isocyclocitral, citronellyloxyacetaldehyde, cortexal-dehyde, cuminaldehyde, cyclamenaldehyde, florhydral, heliotropin, hydratropaldehyde, vanillin, ethylvanillin, benzaldehyde, p-methylbenzaldehyde, 3,4-dimethoxybenzaldehyde, 3- and 4-(4-hydroxy-4-methyl-pentyl)-3-cyclohexene-1-carboxaldehyde (lyral), 2,4-dimethyl-3-cyclohexene-1-carboxaldehyde (triplal), 1-methyl-3-(4- methylpentyl)-3-cyclohexenecarboxaldehyde (vernaldehyde) or p-methylphenoxyacetaldehyd-e (Xi aldehyde).

17. The process of claim 7, further comprising applying the mixture of developer mass and ammoniacal dye solution to hair.

18. The process of claim 8, further comprising applying the mixture of developer mass and ammoniacal dye solution to hair.

* * * * *